United States Patent [19]

Tice

[11] Patent Number: 5,723,414
[45] Date of Patent: Mar. 3, 1998

[54] 5-ARYL-ISOXAZOLINONES AND HERBICIDAL USE THEREOF

[75] Inventor: Colin Michael Tice, Elkins Park, Pa.

[73] Assignee: Rohm and Haas Company, Philadelphia, Pa.

[21] Appl. No.: 786,573

[22] Filed: Jan. 21, 1997

[51] Int. Cl.$^6$ .................. A01N 43/26; A01N 43/40; C07D 413/04
[52] U.S. Cl. .................. 504/252; 504/271; 546/272.1; 548/243
[58] Field of Search .................. 504/252, 271; 546/272.1; 548/243

[56] References Cited

U.S. PATENT DOCUMENTS

| | | | |
|---|---|---|---|
| 5,284,957 | 2/1994 | Huff | 548/112 |
| 5,409,946 | 4/1995 | Garvey et al. | 514/372 |

OTHER PUBLICATIONS

Tomita, K., Sugai, S., Kobayashi, T., and Murakami, T., Chem. Pharm. Bull., 27(10) 2398–2404, 1979.
Sato, K., Sugai, S. and Tomita, K., Agric. Biol. Chem., 50(7), 1831–1837, 1986.

*Primary Examiner*—Joseph McKane
*Attorney, Agent, or Firm*—Clark R. Carpenter

[57] ABSTRACT

A class of 5-aryl-isoxazolinones and compositions thereof which are useful in the control of weeds is of the general formula

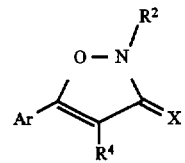

wherein Ar is a substituted or unsubstituted aryl or heteroaryl;

$R^2$ is alkyl, cycloalkyl, alkenyl, cycloalkenyl, alkynyl or alkoxyalkyl, all of which may be substituted with one or more halogen atoms;

$R^4$ is alkynyl or alkoxyalkyl, both of which may be substituted with one or more halogen atoms; and X is an oxygen or a sulfur atom.

16 Claims, No Drawings

5-ARYL-ISOXAZOLINONES AND HERBICIDAL USE THEREOF

This is a nonprovisional application of prior provisional application Ser. No. 60/010,498, filed Jan. 24, 1996, now abandoned.

The need continues for novel and improved herbicidal compounds and compositions. This is particularly so since the targets of herbicides can become resistant to known herbicides over time and after use of such compositions. Additionally, economic and environmental considerations can favor herbicides having different modes of performance than those currently used. This invention relates to novel 5-aryl-isoxazolinones, compositions comprising 5-aryl-isoxazolinones, and the use of 5-aryl-isoxazolinones and compositions thereof as broad spectrum herbicides which are effective against both monocot and dicot weed species in either preemergence or postemergence applications. This invention also teaches methods of preparing these compounds as well as methods of using the compounds as herbicides.

Tomita et al., *Chem. Pharm. Bull.*, 27 (10), 2398–2404 (1979) disclose various isoxazolinones, but the substituent pattern is not related to that of the present invention nor is any herbicidal utility taught. Similarly, Sato et al., *Agric. Biol. Chem.*, 50 (7), 1831–1837 (1986) disclose an isoxazolinone, but again the substituent pattern is not related to that of the present invention nor is any herbicidal utility taught.

One embodiment of this invention relates to 5-aryl-isoxazolinone compounds having the general formula

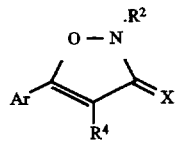

wherein

Ar is a substituted or unsubstituted aryl or heteroaryl;

$R^2$ is alkyl, cycloalkyl, alkenyl, cycloalkenyl, alkynyl or alkoxyalkyl, all of which may be substituted with one or more halogen atoms;

$R^4$ is alkynyl or alkoxyalkyl, both of which may be substituted with one or more halogen atoms; and X is an oxygen or a sulfur atom.

In a preferred embodiment of this invention, Ar is furyl, phenyl, naphthyl, pyridyl or thienyl, or furyl, phenyl, naphthyl, pyridyl or thienyl substituted with up to three substituents independently selected from bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, halo$(C_2-C_{12})$alkenyl, halo$(C_2-C_6)$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl, hydroxyimino and nitro.

Preferred phenyl groups are phenyl, 3-methylphenyl, 3-methoxyphenyl, 3-nitrophenyl, 4-fluorophenyl, 4-chlorophenyl, 3-trifluoromethylphenyl, 3-bromophenyl, 3-chlorophenyl, 3-fluorophenyl, 3-trifluoromethoxyphenyl, 3-cyanophenyl, 3-(1,3-dioxolan-2-yl)phenyl, 3-(hydroxyimino)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl and 3,4,5-trifluorophenyl. More preferred phenyl groups are phenyl, 3-fluorophenyl, 3,5-difluorophenyl, 3,5-dichlorophenyl, 3-chloro-4-fluorophenyl and 3-chlorophenyl.

Preferred pyridyl groups are 6-chloro-2-pyridyl, 3-pyridyl, 5-bromo-3-pyridyl, 5,6-dichloro-3-pyridyl, 5-fluoro-3-pyridyl, 5-chloro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 4,6-dichloro-2-pyridyl, 2,6-difluoro-4-pyridyl and 2,6-dichloro-4-pyridyl. More preferred pyridyl groups are 2-chloro-4-pyridyl, 2-fluoro-4-pyridyl, 5-fluoro-3-pyridyl, 5-chloro-3-pyridyl, 2,6-dichloro-4-pyridyl and 4,6-dichloro-2-pyridyl.

Preferred furyl groups are 2-furyl and 3-furyl.

A preferred naphthyl group is 2-naphthyl.

Preferred thienyl groups are 2-thienyl, 3-thienyl, 4-chloro-2-thienyl, 5-chloro-2-thienyl, 5-chloro-3-thienyl and 2,5-dichloro-3-thienyl. More preferred thienyl groups are 2-thienyl and 5-chloro-3-thienyl.

Preferred $R^2$ groups are $(C_1-C_8)$alkyl, cyclo$(C_3-C_8)$alkyl, $(C_3-C_8)$alkenyl, cyclo$(C_3-C_8)$alkenyl, $(C_3-C_8)$alkynyl and $(C_1-C_4)$alkoxy$(C_1-C_4)$alkyl, all of which may be substituted with one or more halogen atoms. More preferred $R^2$ groups are $(C_1-C_5)$alkyl, $(C_3-C_5)$alkenyl, $(C_3-C_5)$alkynyl and $(C_1-C_2)$alkoxy$(C_1-C_2)$alkyl, all of which may be substituted with one or more halogen atoms. Even more preferred $R^2$ groups are methyl, ethyl, n-propyl, isopropyl, tert-butyl, allyl, propargyl, 1-methylpropargyl, 2,2,2-trifluoroethyl and methoxymethyl. Most preferred $R^2$ groups are methyl, ethyl, n-propyl, isopropyl, tert-butyl, allyl and propargyl.

Preferred $R^4$ groups are $(C_3-C_6)$alkynyl and $(C_1-C_3)$alkoxy$(C_1-C_3)$alkyl, both of which may be substituted with one or more halogen atoms. More preferred $R^4$ groups are $(C_3-C_4)$alkynyl, $(C_1-C_2)$alkoxy$(C_1-C_2)$alkyl and 3-iodopropargyl. The most preferred $R^4$ group is propargyl.

The preferred X is an oxygen atom.

A second embodiment of this invention relates to herbicidal compositions comprising 5-aryl-isoxazolinone compounds having the general formula (I) and an agronomically acceptable carrier.

A third embodiment of this invention relates to a method of controlling a weed comprising applying a herbicidally effective amount of a composition comprising 5-aryl-isoxazolinone compounds having the general formula (I) and an agronomically acceptable carrier to the weed, to the locus of the weed or to the growth medium of said weed.

The general experimental procedure employed to synthesize representative 5-aryl-isoxazolinone compounds of this invention is to treat an α-substituted-β-ketoester (ArCOCH($R^4$)CO$_2$R) with a base such as an alkali metal hydroxide or alkoxide followed by a hydroxylamine ($R^2$NHOH) in a mixture of water and alcohol at −10° to −40° C., wherein Ar, $R^2$ and $R^4$ are as described previously and R is an alkyl group. The mixture is then acidified by addition of a concentrated mineral acid and heated at reflux to give the desired isoxazolinone. A specific example for the preparation of 2-methyl-5-phenyl-4-propargylisoxazolin-3-one (Compound 1) follows:

Preparation of 2-methyl-5-phenyl-4-propargylisoxazolin-3-one (Compound 1)

A stirred solution of 0.28 g (7.0 mmol) of NaOH in 3 mL of water and 7 mL of methanol was cooled to −30° C. and and a solution of 1.42 g (6.2 mmol) of ethyl α-benzoyl-α-propargylacetate in 2 mL of methanol was added dropwise over 2 min. The mixture was stirred at −30° C. for 10 min and a precooled slurry of 0.54 g (13.5 mmol) of NaOH and 1.02 g (12.2 mmol) of N-methylhydroxylamine in 1.5 mL of water was added in one portion. After the mixture had been stirred at −30° C. for 2 h, a 2 mL portion of conc HCl was added and the mixture was heated at reflux for 1 h. The mixture was allowed to cool to room temperature, diluted-with 150 mL of ether, washed with 50 mL of water and 50 mL of saturated aqueous NaHCO$_3$ and dried. Removal of the solvent on the rotovap left 1.09 g of an oil which was purified by flash chromatography on a column of 30 g of silica gel eluted successively with 100 mL portions of 20, 30, 40, 50, 60, 70 and 80% ether in hexanes to afford 0.46 g of 2-methyl-5-phenyl-4-propargylisoxazolin-3-one (Compound 1) as a white solid, m.p. 85°–87° C.

Table I lists representative compounds synthesized and used in the present invention. These compounds are provided merely to illustrate their methods of preparation and their use in the method of the present invention. Table II lists additional compounds of this invention which may be synthesized using the general experimental procedure defined previously. The compounds listed in Tables I and II are not intended to limit the scope of the invention which is defined by the claims.

soil either before, during or after seeding, but before the crop emerges. Postemergence herbicides are applied after the plants have emerged and during their growth period. The embodied materials generally show selectivity to several agronomically important crops such as corn, cotton, rice, soybean, sugarbeet, sunflower, peanut and wheat.

Under some conditions the compounds of the invention may be incorporated into the soil or other growth medium prior to planting a crop. This incorporation may be by any convenient means, including mixing with the soil, applying the compound to the surface of the soil and then dishing or dragging into the soil to the desired depth, or by employing a liquid carrier.

The 5-aryl-isoxazolinones of the present invention can be applied to various loci such the soil or the foliage. For such purposes these compounds can be used in the technical or pure form as prepared, as solutions or as formulations. The compounds are usually taken up in a carrier or are formulated so as to render them suitable for subsequent dissemination as herbicides. For example, these chemical agents can

TABLE I

Structures of Prepared Compounds

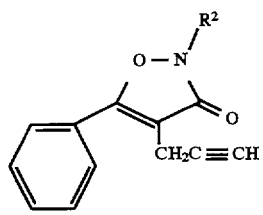

| Cmpd. No. | R² | M.P. °C. | 1H—NMR (CDCl$_3$)δ |
|---|---|---|---|
| 1 | methyl | 85–87 | 2.1(1H, t), 3.4(2H, d), 3.6(3H, s), 7.55(3H, m), 7.8(2H, m) |
| 2 | n-propyl | oil | 1.0(3H, t), 1.85 (2H, m), 2.05(1H, t), 3.4(2H, d), 4.0(2H, t), 7.55(3H, m), 7.8(2H, m) |

TABLE II

Structures of Additional Compounds

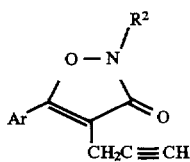

| Cmpd. No. | R² | Ar |
|---|---|---|
| 3 | isopropyl | phenyl |
| 4 | tert-butyl | phenyl |
| 5 | propargyl | phenyl |
| 6 | isopropyl | 3-fluorophenyl |
| 7 | n-propyl | 3-chlorophenyl |
| 8 | 2,2,2-trifluoroethyl | 3,5-dichlorophenyl |
| 9 | n-propyl | 2-chloro-4-pyridyl |
| 10 | ethyl | 2,6-dichloro-4-pyridyl |

The 5-aryl-isoxazolinone compounds of this invention are useful as preemergence and postemergence herbicides. In general, they require lower doses to control weeds preemergence. Preemergence herbicides are usually applied to the be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual." Allured Publishing Company, Ridgewood, N.J., U.S.A.

The 5-aryl-isoxazolinones can be applied as herbicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and weeds to be controlled, but the preferred effective amount is usually from about 0.011 kg. to about 11.2 kg. per hectare of the active ingredient.

As a soil treatment the chemical can be incorporated in the soil or applied to the surface usually at a rate of from about 0.011 kg. to about 11.2 kg. per hectare. As a foliar spray, the toxicant is usually applied to growing plants at a rate of from about 0.011 kg. to about 11.2 kg. per hectare.

The 5-aryl-isoxazolinones of the invention can also be mixed with fertilizers or fertilizing materials before their application. In one type of solid fertilizing composition in which the 5-aryl-isoxazolinones can be used, particles of a fertilizer or fertilizing ingredients, such as ammonium sulfate, ammonium nitrate, or ammonium phosphate, can be coated with one or more of the compounds. The solid compounds and solid fertilizing material can also be admixed in mixing or blending equipment, or they can be incorporated with fertilizers in granular formulations. Any relative proportion of fertilizer can be used which is suitable for the crops and weeds to be treated. The 5-aryl-isoxazolinone will commonly be from about 5% to about 25% of the fertilizing composition. These compositions provide fertilizing materials which promote the rapid growth of desired plants, and at the same time control the growth of undesired plants.

For some applications, one or more other herbicides may be added of the herbicides of the present invention, thereby providing additional advantages and effectiveness. When mixtures of herbicides are employed, the relative proportions which are used will depend upon the relative efficacy of compounds in the mixture with respect to the plants to be treated. Examples of other herbicides which can be combined with those of the present invention include:

CARBOXYLIC ACIDS AND DERIVATIVES 2,3,6-trichlorobenzoic acid and its salts;
2,3,5,6-tetrachlorobenzoic acid and its salts;
2-methoxy-3,5,6-trichlorobenzoic acid and its salts;
2-methoxy-3,6-dichlorobenzoic acid and its salts;
2-methyl-3,6-dichlorobenzoic acid and its salts;
2,3-dichloro-6-methylbenzoic acid and its salts;
2,4-dichlorophenoxyacetic acid and its salts and esters;
2,4,5-trichlorophenoxyacetic acid and its salts and esters;
2-methyl-4-chlorophenoxyacetic acid and its salts and esters;
2-(2,4,5-trichlorophenoxy)propionic acid and its salts and esters;
4-(2,4-dichlorophenoxy)butyric acid and its salts and esters;
4-(2-methyl-4-chlorophenoxy)butyric acid and its salts and esters;
2,3,6-trichlorophenylacetic acid and its salts;
3,6-endoxohexahydrophthalic acid and its salts;
dimethyl 2,3,5,6-tetrachloroterephthalate; trichloroacetic acid and its salts;
2,2-dichloropropionic acid and its salts;
2,3-dichloroisobutyric acid and its salts;
isopropylammonium 2-(4-isopropyl-4-methyl-5-oxo-2-imidazolin-2-yl)nicotinate;
2-[4,5-dihydro-4-methyl-4-(1-methylethyl)-5-oxo-1H-imidazol-2-yl]-3-quinolinecarboxylic acid;
6-(4-isopropyl-4-methyl-5-oxo-2-imidazolin-2-yl)-m-toluic acid, methyl ester;
6-(4-isopropyl-4-methyl-5-oxo-2-imidazolin-2-yl)-p-toluic acid, methyl ester;
N-(phosphomethyl)glycine isopropylammonium salt;
[3,5,6-trichloro-(2-pyridinyl)oxy]acetic acid;
3,7-dichloro-8-quinolinecarboxylic acid;
ammonium DL-homoalanin-4-yl(methyl)phosphinate;

CARBAMIC ACID DERIVATIVES ethyl N,N-di(n-propyl)thiolcarbamate;
n-propyl N,N-di(n-propyl)thiolcarbamate;
ethyl N-ethyl-N-(n-butyl)thiolcarbamate;
n-propyl N-ethyl-N-(n-butyl)thiolcarbamate;
2-chloroallyl N,N-diethyldithiocarbamate;
isopropyl N-phenylcarbamate;
isopropyl N-(m-chlorophenyl)carbamate;
4-chloro-2-butynyl-N-(m-chlorophenyl)carbamate;
methyl N-(3,4-dichlorophenyl)carbamate;
dinitro-o-(sec-butyl)phenol and its salts;
pentachlorophenol and its salts
S-(4-chlorobenzyl)-N,N-diethylthiolcarbamate;

SUBSTITUTED UREAS 2-chloro-N-[(4-methoxy-6-methyl-1,3,5-triazin-2-yl)aminocarbonyl]benzenesulfonamide;
3-(3,4-dichlorophenyl)-1,1-dimethylurea;
3-phenyl-1,1-dimethylurea;
3-(3,4-dichlorophenyl)-3-methoxy-1,1-dimethylurea;
3-(4-chlorophenyl)-3-methoxy-1,1-dimethylurea;
3-(3,4-dichlorophenyl)-1-n-butyl-1-methylurea;
3-(3,4-dichlorophenyl)-1-methoxy-1-methylurea;
3-(4-chlorophenyl)-1-methoxy-1-methylurea;
3-(3,4-dichlorophenyl)-1,1,3-trimethylurea;
3-(3,4-dichlorophenyl)diethylurea;
N-(4-isopropylphenyl)-N,N'-dimethylurea;
dichloral urea;
methyl 2-[[[[(4,6-dimethyl-2-pyrimidinyl)amino]carbonyl]amino]sulfonyl]benzoate;
N-((6-methoxy-4-methyl-1,3,5-triazin-2-yl)aminocarbonyl)-2-(2-chloroethoxy)-benzenesulfonamide;
2-[[[(4-chloro-6-methoxypyrimidine-2-yl) aminocarbonyl]amino]sulfonyl]benzoic acid, ethyl ester;
methyl 2-[[[[(4-methoxy-6-methyl-1,3,5-triazin-2-yl)amino]carbonyl]amino]sulfonyl]benzoate;
methyl 3-[[(4-methoxy-6-methyl-1,3,5-triazin-2-yl)aminocarbonyl]aminosulfonyl]-2-thiophenecarboxylate;
methyl 2-[[[[(4,6-dimethoxypyrimidin-2-yl)amino]carbonyl]amino]sulfonyl]methyl]benzoate;
methyl 2-[[[[(4-methoxy-6-methyl-1,3,5-triazin-2-yl)methylamino]carbonyl]amino]sulfonyl]benzoate;

SUBSTITUTED TRIAZINES 2-chloro-4,6-bis(ethylamino)-s-triazine;
2-chloro-4-ethylamino-6-isopropylamino-s-triazine;
2-chloro-4,6-bis(3-methoxy-n-propylamino)-s-triazine;
2-methoxy-4,6-bis(isopropylamino)-s-triazine;
2-chloro-4-ethylamino-6-(3-methoxy-n-propylamino)-s-triazine;
2-methylmercapto-4,6-bis(isopropylamino)-s-triazine;
2-methylmercapto-4,6-bis(ethylamino)-2-triazine;
2-methylmercapto-4-ethylamino-6-isopropylamino-s-triazine;
2-chloro-4,6-bis(isopropylamino)-s-triazine;
2-methoxy-4-ethylamino-6-isopropylamino-s-triazine;
2-methylmercapto-4-(2-methoxyethylamino)-6-isopropylamino-s-triazine;
4-amino-6-(t-butyl)-3-(methylthio)-1,2,4-triazine-5(4H)-one;

DIPHENYL ETHER DERIVATIVES 2,4-dichloro-4'-nitrodiphenyl ether;
2,4,6-trichloro-4'-nitrodiphenyl ether;
2,4-dichloro-6-fluoro-4'-nitrodiphenyl ether;
3-methyl-4'-nitrodiphenyl ether;
3,5-dimethyl-5'-nitrodiphenyl ether;
2,4'-dinitro-4-(trifluoroethyl)diphenyl ether;
2,4-dichloro-3'-methoxy-4'-nitrodiphenyl ether;
sodium 5-(2-chloro-4-(trifluoroethyl)phenoxy)-2-nitrobenzoate;
2-chloro-1-(3-ethoxy-4-nitrophenoxy)-4-(trifluoroethyl)benzene;
1-(carboethoxy)ethyl 5-[2-chloro-4-(trifluoromethyl) phenoxy]-2-nitrobenzoate;
5-[2-chloro-4-(trifluoromethyl)phenoxyl]-N-(methylsulphony)-2-nitrobenzamide;

ANILIDES 2-chloro-N-(2-ethyl-6-methylphenyl)-N-(2-methoxy-1-methylethyl)acetamide;
2-chloro-2',6'-diethyl-N-(2-propyloxyethyl)acetanilide;
N-(3,4-dichlorophenyl)propionamide;
N-(3,4-dichlorophenyl)methacrylamide;
N-(3-chloro-4-methylphenyl)-2-methylpentanamide;
N-(3,4-dichlorophenyl)trimethylacetamide;
N-(3,4-dichlorophenyl)-α,α-dimethylvaleramide;
N-isopropyl-N-phenylchloroacetamide;
N-n-butoxymethyl-N-(2,6-diethylphenyl)chloroacetamide;
N-methoxymethyl-N-(2,6-diethylphenyl)chloroacetamide;

OXYPHENOXY HERBICIDES 2-(4-(2,4-dichlorophenoxy)phenoxy)methyl propionate;
methyl 2-(4-(3-chloro-5-(trifluoromethyl)-2-pyridinyloxy)phenoxy)propanoate;
butyl (R)-2-[4-[5-(trifluoromethyl)-2-pyridinyloxy]phenoxy]propionate;
ethyl 2-[4-[(6-chloro-2-benzoxazolyl)oxy]phenoxy]propanoate;
butyl 2-[4-[[5-(trifluoromethyl)-2-pyridinyl]oxy]phenoxy]propionate;
2-[4-[(6-chloro-2-quinoxalinyl)oxy]phenoxy]propionic acid, ethyl ester;

URACILS 5-bromo-3-s-butyl-6-methyluracil;
5-bromo-3-cyclohexyl-1,6-dimethyluracil;
3-cyclohexyl-5,6-trimethyleneuracil;
5-bromo-3-isopropyl-6-methyluracil;
3-tert-butyl-5-chloro-6-methyluracil;

NITRILES 2,6-dichlorobenzonitrile;
diphenylacetonitrile;
3,5-dibromo-4-hydroxybenzonitrile;
3,5-diiodo-4-hydroxybenzonitrile;

OTHER ORGANIC HERBICIDES 2-chloro-N,N-diallylacetamide;
N-(1,1-dimethyl-2-propynyl)-3,5-dichlorobenzamide;
maleic hydrazide;
3-amino-1,2,4-triazole;
monosodium methanearsonate;
disodium methanearsonate;
N,N-dimethyl-α,α-diphenylacetamide;
N-N-di(n-propyl)-2,6-dinitro-4-(trifluoromethyl)aniline;
N,N-di(n-propyl)-2,6-dinitro-4-methylaniline;
N,N-di(n-propyl)-2,6-dinitro-4-methylsulfonylaniline;
O-(2,4-dichlorophenyl)-O-methyl isopropylphosphoramidothioate;
4-amino-3,5,6-trichloropicolinic acid;
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;
6,7-dihydrodipyridol[1,2-a:2',1'-c]pyrazidiium salts;
1,1'-dimethyl-4,4'-bipyridinium salts;
3,4,5,6-tetrahydro-3,5-dimethyl-2-thio-2H-1,3,5-thiadiazine;
2-[1-(ethoxyimino)butyl]-5-[s-(ethylthio)propyl]-3-hydroxy-2-cyclohexen-1-one;
2-(2-chlorophenyl)methyl-4,4-dimethyl-3-isoxazolidinone;
N-(1-ethylpropyl)-3,4-dimethyl-2,6-dinitrobenzamide;
4-chloro-5-(methylamino)-2-(α,α,α-trifluoro-m-toluyl)-3-(2H)-pyridazinone;
2-(3,5-dichlorophenyl)-2-(2,2,2-trichloromethyl)oxirane.

When mixtures of herbicides are employed, the relative proportions which are used will depend upon the crop to be treated and the degree of selectivity in weed control desired.

The herbicidal activity of the 5-aryl-isoxazolinones of the present invention towards a number of common weeds was evaluated using a greenhouse method of testing. Using the greenhouse test methods described below, the 5-aryl-isoxazolinone compounds 1 and 2 of the present invention were evaluated for control of weeds selected from the following:

| Common Name | Code | Scientific name |
|---|---|---|
| Monocots | | |
| Barnyardgrass | (BYG) | Echinochloa crus-galli |
| Green Foxtail | (FOX) | Setaria viridis |
| Johnsongrass | (JON) | Sorghum halepense |
| Yellow Nutsedge | (NUT) | Cyperus esculentus |
| Wild Oats | (WO) | Avena fatua |
| Dicots | | |
| Marigold | (MA) | Tagetes minuta |
| Cocklebur | (CKL) | Xanthium strumarium |
| Morningglory | (MG) | Ipomoea spp. |
| Pigweed | (PIG) | Amaranthus retroflexus |
| Smartweed | (SMT) | Polygonum lapathifolium |
| Velvetleaf | (VEL) | Abutilon theophrasti |

Seeds of selected plants were planted in flats or pots. For preemergence tests, immediately after planting, the test compound was sprayed directly onto the soil surface. The flats or pots were placed in the greenhouse and then watered. For postemergence tests, the seeds were allowed to germinate and grow for 10 to 21 days. Before application, each series of test plants was selected for uniformity, size and stage of development. The test plants were then treated with the test compound, returned to the greenhouse and watered.

The compound to be evaluated was dissolved in an appropriate solvent, usually acetone, and sprayed over the flats or pots using a carrier volume equivalent to 234 or 268 liters per hectare at the rate of application in grams per hectare (g/Ha) specified in Table III. About two or three weeks after application of the test compound, the stage of growth of the plant was observed. Each species was evaluated on a scale of 0–100 in which 0 equals no activity and 100 equals total control.

TABLE 111

| GREENHOUSE DATA | | | | | | |
|---|---|---|---|---|---|---|
| Cmpd. No. | TREAT. TYPE | g/Ha | CKL | MG | PIG | SMT | VEL |
| 1 | PRE | 4800 | 0 | 0 | 100 | no test | 100 |
|  | POST | 4800 | 0 | 37 | 17 | 37 | 25 |
| 2 | PRE | 4800 | 0 | 100 | 100 | 100 | 50 |
|  | POST | 4800 | 0 | 25 | 0 | 10 | 0 |

| Cmpd. No. | TREAT. TYPE | g/Ha | BYG | FOX | JON | NUT | WO |
|---|---|---|---|---|---|---|---|
| 1 | PRE | 4800 | 90 | 98 | 27 | 71 | 17 |
|  | POST | 4800 | 0 | 25 | 0 | 0 | 0 |
| 2 | PRE | 4800 | 85 | 45 | 85 | 75 | 20 |
|  | POST | 4800 | 10 | 0 | 0 | 0 | 0 |

PRE = Preemergence Application
POST = Postemergence Application

It is to be understood that changes and variations in this invention may be made without departing from the spirit and scope of this invention as defined by the appended claims.

I claim:
1. A compound of the formula

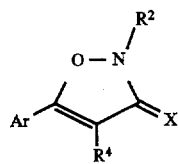

wherein
Ar is a substituted or unsubstituted aryl or heteroaryl;
$R^2$ is alkyl, cycloalkyl, alkenyl, cycloalkenyl, alkynyl or alkoxyalkyl, all of which may be substituted with one or more halogen atoms;
$R^4$ is alkynyl or alkoxyalkyl, both of which may be substituted with one or more halogen atoms; and
X is an oxygen or a sulfur atom.

2. The compound of claim 1 wherein Ar is furyl, phenyl, naphthyl, pyridyl or thienyl, or furyl, phenyl, naphthyl, pyridyl or thienyl substituted with up to three substituents independently selected from bromo, chloro, fluoro, $(C_1-C_{12})$ alkyl, cyclo$(C_3-C_8)$alkyl, $(C_2-C_{12})$alkenyl, cyclo$(C_3-C_8)$ alkenyl, $(C_2-C_{12})$alkynyl, halo$(C_1-C_{12})$alkyl, halo$(C_2-C_{12})$ alkenyl, halo$(C_2-C_6)$alkynyl, $(C_1-C_{12})$alkoxy, $(C_1-C_{12})$ alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen $(C_2-C_{12})$alkynyl, cyano, halo$(C_1-C_{12})$alkoxy, 1,3-dioxalan-2-yl, hydroxyimino and nitro.

3. The compound of claims 1 or 2 wherein Ar is phenyl, 3-methylphenyl, 3-methoxyphenyl, 3-nitrophenyl, 4-fluorophenyl, 4-chlorophenyl, 3-trifluoromethylphenyl, 3-bromophenyl, 3-chlorophenyl, 3-fluorophenyl, 3-trifluoromethoxyphenyl, 3-cyanophenyl, 3-(1,3-dioxolan-2-yl)phenyl, 3-(hydroxyimino)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, 3,4,5-trifluorophenyl, 6-chloro-2-pyridyl, 3-pyridyl, 5-bromo-3-pyridyl, 5,6-dichloro-3-pyridyl, 5-fluoro-3-pyridyl, 5-chloro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 4,6-dichloro-2-pyridyl, 2,6-difluoro-4-pyridyl, 2,6-dichloro-4-pyridyl, 2-furyl, 3-furyl, 2-naphthyl, 2-thienyl, 3-thienyl, 4-chloro-2-thienyl, 5-chloro-2-thienyl, 5-chloro-3-thienyl or 2,5-dichloro-3-thienyl.

4. The compound of claim 3 wherein Ar is phenyl, 3-fluorophenyl, 3,5-difluorophenyl, 3,5-dichlorophenyl, 3-chloro-4-fluorophenyl, 3-chlorophenyl, 2-chloro-4-pyridyl, 2-fluoro-4-pyridyl, 5-fluoro-3-pyridyl, 5-chloro-3-pyridyl, 2,6-dichloro-4-pyridyl, 4,6-dichloro-2-pyridyl, 2-thienyl or 5-chloro-3-thienyl.

5. The compound of claims 1 or 2 wherein $R^2$ is $(C_1-C_8)$ alkyl, cyclo$(C_3-C_8)$alkyl, $(C_3-C_8)$alkenyl, cyclo$(C_3-C_8)$ alkenyl, $(C_3-C_8)$alkynyl or $(C_1-C_4)$alkoxy$(C_1-C_4)$alkyl, all of which may be substituted with one or more halogen atoms.

6. The compound of claim 5 wherein $R^2$ is $(C_1-C_5)$alkyl, $(C_3-C_5)$alkenyl, $(C_3-C_5)$alkynyl or $(C_1-C_2)$alkoxy$(C_1-C_2)$ alkyl, all of which may be substituted with one or more halogen atoms.

7. The compound of claim 6 wherein $R^2$ is methyl, ethyl, n-propyl, isopropyl, tert-butyl, allyl, propargyl, 1-methylpropargyl, 2,2,2-trifluoroethyl or methoxymethyl.

8. The compound of claim 7 wherein $R^2$ is methyl, ethyl, n-propyl, isopropyl, tert-butyl, allyl or propargyl.

9. The compound of claims 1 or 2 wherein $R^4$ is $(C_3-C_6)$ alkynyl or $(C_1-C_3)$alkoxy$(C_1-C_3)$alkyl, both of which may be substituted with one or more halogen atoms.

10. The compound of claim 9 wherein $R^4$ is $(C_3-C_4)$ alkynyl, $(C_1-C_2)$alkoxy$(C_1-C_2)$alkyl or 3-iodopropargyl.

11. The compound of claim 10 wherein $R^4$ is propargyl.

12. The compound of claims 1 or 2 wherein X is an oxygen atom.

13. The compound of claims 1 or 2 wherein

Ar is phenyl, 3-methylphenyl, 3-methoxyphenyl, 3-nitrophenyl, 4-fluorophenyl, 4-chlorophenyl, 3-trifluoromethylphenyl, 3-bromophenyl, 3-chlorophenyl, 3-fluorophenyl, 3-trifluoromethoxyphenyl, 3-cyanophenyl, 3-(1,3-dioxolan-2-yl)phenyl, 3-(hydroxyimino)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, 3,4,5-trifluorophenyl, 6-chloro-2-pyridyl, 3-pyridyl, 5-bromo-3-pyridyl, 5,6-dichloro-3-pyridyl, 5-fluoro-3-pyridyl, 5-chloro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 4,6-dichloro-2-pyridyl, 2,6-difluoro-4-pyridyl, 2,6-dichloro-4-pyridyl, 2-furyl, 3-furyl, 2-naphthyl, 2-thienyl, 3-thienyl, 4-chloro-2-thienyl, 5-chloro-2-thienyl, 5-chloro-3-thienyl or 2,5-dichloro-3-thienyl;

$R^2$ is methyl, ethyl, n-propyl, isopropyl, tert-butyl, allyl, propargyl, 1-methylpropargyl, 2,2,2-trifluoroethyl or methoxymethyl;

$R^4$ is $(C_3-C_4)$alkynyl, $(C_1-C_2)$alkoxy$(C_1-C_2)$alkyl or 3-iodopropargyl; and X is an oxygen atom.

14. The compound of claim 13 wherein

Ar is phenyl, 3-fluorophenyl, 3,5-difluorophenyl, 3,5-dichlorophenyl, 3-chloro-4-fluorophenyl, 3-chlorophenyl, 2-chloro-4-pyridyl, 2-fluoro-4-pyridyl, 5-fluoro-3-pyridyl, 5-chloro-3-pyridyl, 2,6-dichloro-4-pyridyl, 4,6-dichloro-2-pyridyl, 2-thienyl or 5-chloro-3-thienyl;

$R^2$ is methyl, ethyl, n-propyl, isopropyl, tert-butyl, allyl or propargyl; and $R^4$ is propargyl.

15. A herbicidal composition comprising a 5-aryl-isoxazolinone compound of claims 1 or 2 and an agronomically acceptable carrier.

16. A method of controlling a weed comprising applying a herbicidally effective amount of a composition comprising a 5-aryl-isoxazolinone compound of claims 1 or 2 and an agronomically acceptable carrier to the weed, to the locus of the weed or to the growth medium of said weed.

* * * * *